United States Patent
Zin et al.

(10) Patent No.: US 7,220,597 B2
(45) Date of Patent: May 22, 2007

(54) ASSAY TEST DEVICE AND METHOD OF MAKING SAME

(76) Inventors: Benedict L. Zin, 12105 Eleonore Ct., San Diego, CA (US) 92131; Michael Hutchinson, 791 Caley Rd., King of Prussia, PA (US) 19406

( * ) Notice: Subject to any disclaimer, the term of this patent is extended or adjusted under 35 U.S.C. 154(b) by 637 days.

(21) Appl. No.: 10/356,453

(22) Filed: Jan. 30, 2003

(65) Prior Publication Data
US 2004/0152209 A1 Aug. 5, 2004

(51) Int. Cl.
*G01N 33/53* (2006.01)

(52) U.S. Cl. .................. 436/518; 436/514; 436/169; 436/165; 435/7.1; 435/7.92; 435/7.93; 435/7.94; 422/56; 422/58; 422/61; 422/82.05; 422/82.06

(58) Field of Classification Search ............... 436/514, 436/518, 169, 165, 65; 435/7.1, 7.92, 7.93, 435/7.9, 7.94; 422/56, 58, 61, 82.05, 82.06
See application file for complete search history.

(56) References Cited

U.S. PATENT DOCUMENTS

| | | | | |
|---|---|---|---|---|
| 4,995,402 | A | * | 2/1991 | Smith et al. ................ 600/584 |
| 5,580,794 | A | * | 12/1996 | Allen .......................... 436/169 |
| 5,985,675 | A | | 11/1999 | Charm et al. |
| 6,146,590 | A | * | 11/2000 | Mazurek et al. ............ 422/58 |
| 6,150,124 | A | * | 11/2000 | Riedel ......................... 435/14 |
| 6,177,281 | B1 | | 1/2001 | Manita et al. |
| 6,235,241 | B1 | * | 5/2001 | Catt et al. .................... 422/56 |
| 6,241,689 | B1 | * | 6/2001 | Chard et al. ................ 600/584 |
| 6,268,162 | B1 | * | 7/2001 | Phillips et al. ............... 435/14 |
| 6,365,417 | B1 | | 4/2002 | Fleming et al. |
| 6,451,619 | B1 | * | 9/2002 | Catt et al. .................... 436/514 |
| 2003/0018295 | A1 | * | 1/2003 | Henley et al. ............... 604/20 |
| 2004/0082878 | A1 | * | 4/2004 | Baldwin et al. ............. 600/573 |
| 2004/0099266 | A1 | * | 5/2004 | Cross et al. ............ 128/203.12 |
| 2004/0253142 | A1 | * | 12/2004 | Brewster et al. ............. 422/58 |

FOREIGN PATENT DOCUMENTS

EP 0291194 * 11/1988

OTHER PUBLICATIONS

Clearblue Easy Digital Pregnancy Test. www.clearblueeasy.com. May 14, 2003.*

* cited by examiner

*Primary Examiner*—Bao-Thuy L. Nguyen

(57) ABSTRACT

In accordance with certain disclosed embodiments of the present invention, there is provided an assay test device for determining whether a fluid under test contains a certain substance, wherein the device includes a test strip disposed at least partially within a housing for receiving the fluid under test. A sensor mounted on the housing detects the certain substance in the fluid under test received on the test strip to generate an electrical signal indicative of the amount of the substance detected. A processor responds to the signal for determining whether or not the fluid under test contains a predetermined quantity of the certain substance to generate an electrical signal. A display mounted on the housing responds to the output signal to indicate the presence or absence of a predetermined quantity of the certain substance contained within the fluid under test.

14 Claims, 2 Drawing Sheets

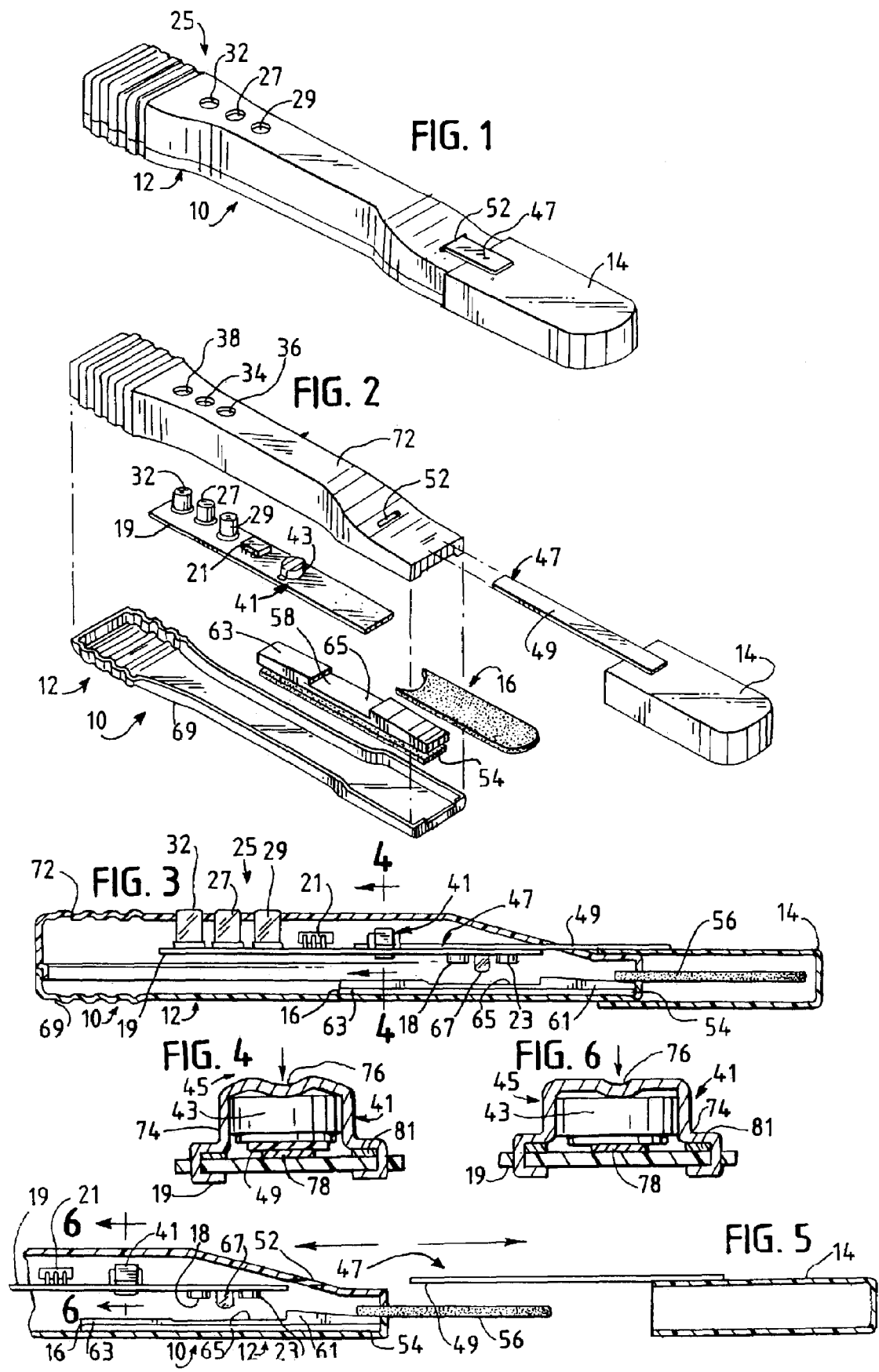

ASSAY TEST DEVICE AND METHOD OF MAKING SAME

RELATED APPLICATIONS

This application incorporates herein by reference U.S. non-provisional patent application, entitled RAPID ASSAY STRIP AND METHOD OF RAPID COMPETITIVE ASSAY, Ser. No. 09/573,717, filed May 12, 2000, now U.S. Pat. No. 6,534,324; U.S. non-provisional patent application, entitled METHOD OF PROCESSING ASSAY TEST RESULTS, Ser. No. 10/356,452, filed Jan. 30, 2003; and published European patent application, entitled DETECTION APPARATUS AND METHOD FOR THE SAME, No. EP 0,962,771A1, filed Jun. 4, 1999.

FIELD OF THE INVENTION

The present invention relates in general to an assay test device and a method of using it. It more particularly relates to a test device and a method of using it for assay test results, such as tests of urine samples for pregnancy, drugs of abuse, tobacco, or other.

BACKGROUND ART

There is no admission that the background art disclosed in this section legally constitutes prior art.

Assay tests have been employed to analyze test samples such as urine samples to determine whether or not they contain substances such as HCG indicating pregnancy, drugs of abuse, or other.

For example, reference may be made to the following United States patents, each of which is incorporated herein by reference:

| PATENT NO. | INVENTOR | ISSUE DATE |
|---|---|---|
| 4,033,723 | Givner, et al. | Jul. 05, 1977 |
| 4,123,509 | Banik, et al. | Oct. 31, 1978 |
| 4,348,207 | Cappel | Sep. 07, 1982 |
| 4,450,239 | Chatterton | May 22, 1984 |
| 4,700,711 | Carlson | Oct. 20, 1987 |
| 5,182,216 | Clayton, et al. | Jan. 29, 1993 |
| 5,580,794 | Allen, et al. | Dec. 3, 1996 |
| 5,656,503 | May, et al. | Aug. 12, 1997 |
| 5,786,220 | Pronovost, et al. | Jul. 28, 1998 |
| 5,837,546 | Allen, et al. | Nov. 17, 1998 |
| 6,063,026 | Schauss, et al. | May 16, 2000 |
| 6,150,178 | Cesarczyk, et al. | Nov. 21, 2000 |
| 6,235,241B1 | Catt, et al. | May 22, 2001 |

Test strips, as disclosed in one or more of the foregoing patents, are employed to receive a test sample such as a urine sample for performing an assay test. For example, a pregnancy test strip has been used to collect a urine sample to react with a reagent to produce a visible line such as a line having a pink/purple color. It is sometimes difficult to make a subjective determination as to the intensity of the color of the line relative to a comparison line. Thus, false positive indications are sometimes possible.

In an attempt to help interpret the results of such assay test, the U.S. Pat. No. 6,235,241B1 discloses a test strip disposed within a casing or housing, and includes a light source with diffusers to illuminate the test strip to help the user to interpret the results of a test. Light sensors on the other side of the test strip detect the light shining through the test strip. However, such a device is complex in its construction, and thus relatively expensive to manufacture.

For the purpose of making a relatively inexpensive assay test device, which can be for single use only, as disclosed in U.S. Pat. Nos. 5,580,794 and 5,873,546, a disposable device includes a test membrane containing a reagent for receiving a liquid test sample. A set of electrodes detects the presence of movement of the sample liquid to activate the device electrically to cause sensors to sense the results of the chemical reaction of the reagent with the test sample. In this regard, as the liquid sample moves toward the electrodes, the reaction is occurring and the results are sensed once the liquid reaches the electrodes. Alternatively, the device may be activated electrically by closing a switch when it is removed from its pouch, and the reaction results are sensed after a specified time.

However, when the electrodes are used, the reaction time may be dependent on the length of time it takes for the movement of the liquid sample along the membrane. Thus, the reaction time may not be precisely controlled and repeatable, and thus accuracy may be adversely affected. When the alternative approach of sensing the reaction results after initially turning on the device, following a time delay, the reaction time is even less precisely controlled, because there is little or no control over when the sample is introduced to the membrane following the activation of the device.

Therefore, it would he highly desirable to have a new and improved testing device and method of using it, which are relatively more accurate in the determination of the test results, while at the same time being relatively inexpensive to manufacture and to use. Thus, such a device and method may, if desired, be employed for a single use, and yet be relatively accurate in its use.

BRIEF DESCRIPTION OF THE DRAWINGS

The following is a brief description of the drawings:

FIG. 1 is a pictorial view of a device which is constructed in accordance with a disclosed embodiment of the present invention;

FIG. 2 is an exploded view of the device of FIG. 1;

FIG. 3 is an enlarged sectional elevational view of the device of FIG. 1;

FIG. 4 is an enlarged sectional view of the device of FIG. 3 taken substantially on line 4-4 thereof;

FIG. 5 is a fragmentary sectional elevational view of the device of FIG. 3, illustrating it with its lid portion being removed;

FIG. 6 is an enlarged sectional view of FIG. 5 taken substantially on line 6-6 thereof.

DETAILED DESCRIPTION OF CERTAIN EMBODIMENTS OF THE INVENTION

Figure 7:
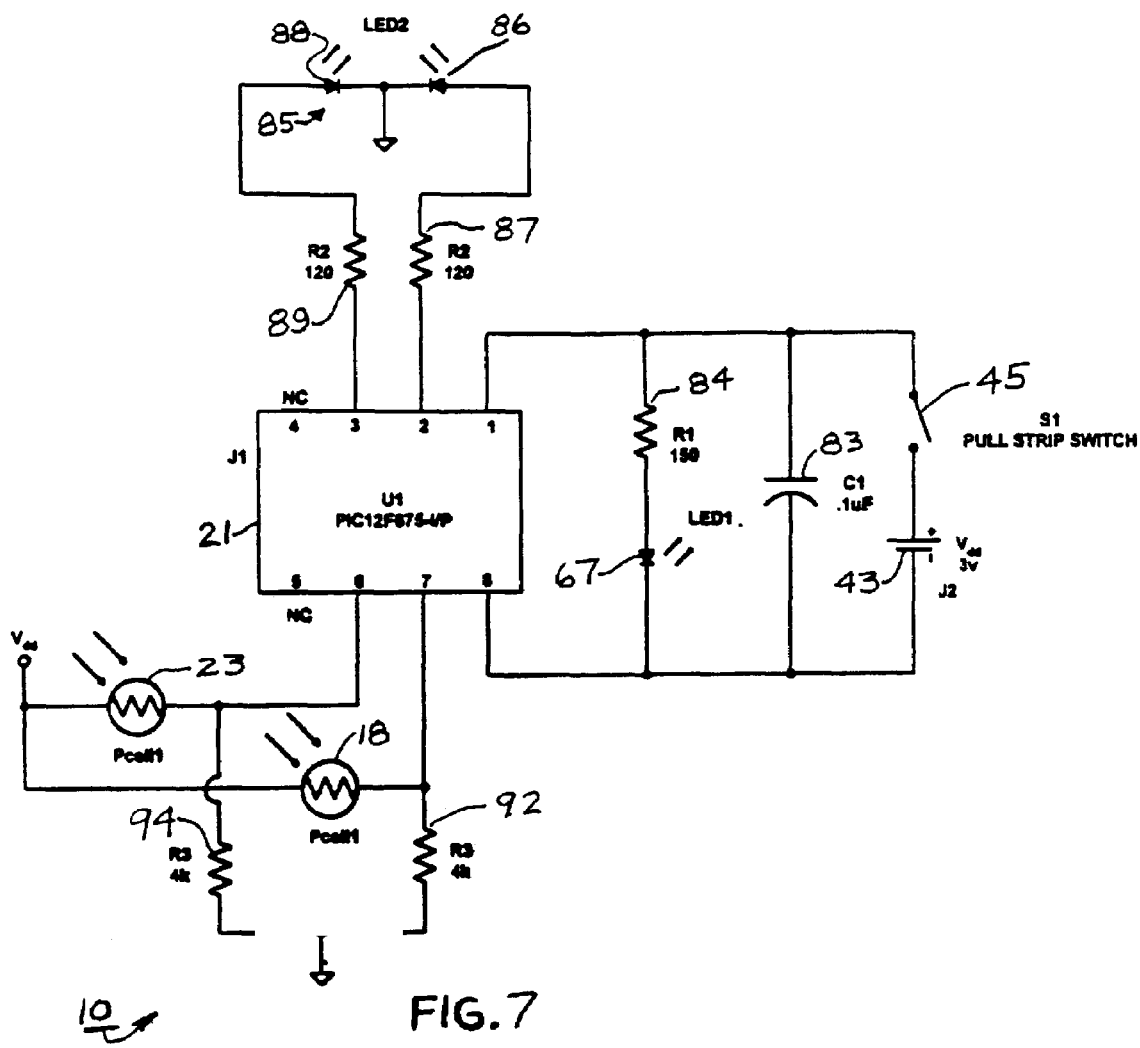
FIG. 7 is a schematic circuit diagram of the device of FIG. 1.

In accordance with certain disclosed embodiments of the present invention, there is provided an assay test device for determining whether a fluid under test contains a certain substance, wherein the device includes a test strip disposed at least partially within a housing for receiving the fluid under test. A sensor mounted on the housing detects the certain substance in the fluid under test received on the test strip to generate an electrical signal indicative of the amount of the substance detected. A processor responds to the signal for determining whether or not the fluid under test contains a predetermined quantity of the certain substance to generate an electric output signal. A display mounted on the housing responds to the output signal to indicate the presence or absence of a predetermined quantity of the certain substance contained within the fluid under test.

According to other embodiments of the invention, the processor delays in activating the reaction sensor until after a predetermined time delay interval. The processor stores the sensor signal at the completion of the time delay interval, and compares the stored sensor signal with stored threshold electric signals to determine whether or not the fluid under test contains a predetermined quantity of the certain substance.

According to other embodiments of the invention disclosed herein, the test strip includes an elongated wick for receiving the fluid under test at one end portion of the test strip. A sample sensor mounted on the housing adjacent to the wick disposed remotely of the fluid receiving end portion detects the presence of the fluid under test to generate an electric signal indicative of the start of the predetermined time delay interval. The test device includes a display element indicating that the device is ready to receive the fluid under test. The display also includes a positive substance indication display element and a negative substance indication display element.

A lid is removably attached to the housing for covering at least a portion of the fluid receiving end portion of the wick so that the lid can be removed from the housing to expose the liquid receiving end portion of the wick. A switch activates the device in response to the removal of the lid from the housing.

Referring now to the drawings, and more particularly to FIGS. 1-6 thereof, there is shown an assay test device 10, which is adapted for determining whether a fluid under test contains a certain substance, and which is constructed in accordance with a disclosed embodiment of the invention. The device 10 includes an elongated housing 12 having a removable lid or cap 14. The housing 12 is adapted to be held in the hand of the user.

An elongated test strip 16 is disposed longitudinally within the housing 12. The test strip may be in the form of the test strip disclosed in the aforementioned European patent application No. EP0,962,771A1. The test strip 16 of the device 10 is initially contemplated to be used for pregnancy testing, but it is to be understood by those skilled in the art, that other different types and kinds of test strips may be employed for other testing purposes, including but not limited to, the testing for drugs of abuse, and other tests.

A sample sensor 18 (FIGS. 3 and 5) is mounted on the underside of a printed circuit board 19 and is disposed opposite the test strip 16 intermediate its end portions for detecting the presence of the sample as it flows along the test strip for generating a signal indicative of the presence of the sample. The sample sensor may be a photo-optic sensor, but it can be other types and kinds of sensors, including magnetic sensors such as Hall effect device. When magnetic sensors are used, then magnetic particles are employed on the test strip.

A processor 21 mounted on the top surface of the printed circuit board 19 is responsive to the sample presence signal from the sample sensor 18 for starting a software timer to generate a time delay interval and for generating a time-out signal at the end if the interval. In this regard, the time delay interval allows for the propagation time of the sample from one end portion to an intermediate portion of the test strip 16 opposite the sensor 18.

As shown in FIGS. 3 and 5, a reaction sensor 23 mounted on the underside of the printed circuit board 19 responds to the time-out signal from the processor 21 for detecting a certain substance in the fluid under test received on the test strip 16 to generate an electrical signal indicative of the amount of the substance detected. In this regard, the reaction sensor is preferably a photo-optic sensor, but it may also be other types and kinds of sensors, including magnetic sensors such as Hall effect devices. When a photo-optic sensor is used, and when the test strip 16 is employed as disclosed in the aforementioned European patent application, a dark line forms on the test strip and is detected by the photo-optic reaction sensor 23.

As indicated in FIGS. 1 and 3, a display generally indicated at 25 includes an amber light emitting diode (LED) 27, a green light emitting diode (LED) 29 and a red light emitting diode (LED) 32 disposed in a row on the top surface of the housing 12, and are positioned within corresponding holes 34, 36 and 38. The display 25 responds to an output signal from the processor 21 for indicating the presence or absence of a predetermined quantity of the certain substance contained within the fluid under test. The processor generates the output signal in response to the signal from the reaction sensor 23. The output signal from the processor is indicative of the presence or absence of at least a predetermined quantity of the substance contained in the sample.

A power supply generally indicated at 41 is mounted on the top surface of the printed circuit board 19, and is preferably in the form of a battery 43 which is connected electrically to the printed circuit board 19 and its components via a switch generally indicated at 45 (FIGS. 4 and 6). A switch actuator 47 preferably in the form of an insulator strip 49 extends through an opening 52 in an angular wall portion of the housing 12 and extends to the switch 45 when the lid 14 is assembled to the housing 12 as shown in FIGS. 1 and 3 When the lid 14 is removed from the housing 12 as indicated in FIG. 5, the actuator 47 is pulled away from the switch 45 as indicated in FIGS. 4 and 6, to cause the battery 43 to be connected electrically to the printed circuit board 19 for energizing the device 10.

In use, in order to start a testing operation by, for example, testing for HCG in a urine sample to indicate whether or not a person is pregnant, the lid 14 is removed from the housing 12 to cause the insulation strip 49 to be pulled out from under the battery 43 to cause the battery to energize the device 10. Once energized, the device 10 causes the amber LED 27 to blink or otherwise to turn on, indicating that the power is on and the device 10 is ready to receive the urine test sample. Should the device not be used after being energized, the amber LED 27 blinks or stays on until the battery becomes exhausted.

The user then applies a urine sample to the test strip 16.

The sample sensor 18 detects the presence of the urine sample once it has migrated along the test strip and the top surface of the test strip turns from a white color to a darker color as a result of being wetted by the urine sample. If the sensor 18 does not respond to the color change, the device 10 does not proceed further in the operation and eventually the battery 43 will become exhausted.

The processor 21 causes a software timer to start a time delay interval with the actuation of the battery 43 and will stop timing once the sample sensor 18 detects the presence of the urine sample, or the timer times out. If the timer times out prior to the sensing of urine sample, the amber LED 27 will start to blink to provide a visual indication that the battery life is near its end.

If the sample sensor 18 detects the presence of the urine sample (even after the amber light commences blinking), the processor 21 responds to an electrical signal from the sample sensor 18 to start another time delay interval based on the performance/optimization of the desired test. In this regard, the time interval is provided to allow sufficient time for the test to develop. For example, for a pregnancy test, there may be a time-out interval of 3 minutes.

Once the processor 21 reaches the end of the time-out interval, the processor 21 causes the reaction sensor 23 to read the intermediate portion of the test strip 16 to detect the presence of a line created by the test reaction. The current value is compared with a stored value of the intensity of the line to determine whether or not the line is present. If the difference is greater than the defined threshold level, the green LED 29 is illuminated, to indicate a positive test result. If the difference is less than the threshold value, the red LED 32 is illuminated by the processor, to indicate a negative test result. Either the green LED 29 or the red LED 32 remains illuminated until the battery dies, or the battery 43 is disconnected from the printed circuit board 19 by means of the switch actuator 47 engaging the switch 45 by replacing the lid 14 on the housing 12.

It is to be understood that the device 10 is contemplated to be a single use device which is relatively accurate in its measurements. However, it will be understood by those skilled in the art that the device 10 may be a multiple use device by permitting the test strip to be replaced with a fresh test strip.

Considering now the test strip 16 in greater detail with reference to FIGS. 3 and 5 of the drawings, the test strip 16 includes a backing strip 54 which has a sample pad or wick 56 extends out of the housing 18 and is covered by the lid 14 when it is assembled to the housing 12. When the lid 14 is removed from the housing 12, the wick 56 is exposed so that the urine sample may be applied thereto. A porous carrier strip 58 has a reagent section or pad 61 affixed to the wick 56, and a fluid absorption section or strip 63 at the opposite end portion thereof. A catching section or line forming zone 65 on the upper surface of the intermediate portion of the porous carrier strip 58 is disposed opposite the reaction sensor 23 where a line is formed once the reaction occurs when human chorionic gonadotropin (HCG) is present in the urine sample indicating that the user is pregnant.

The reagent pad 61 contains the suitable reagent for performing the desired test on the sample. In this regard, the sample is received on the wick 56 and migrates through the reagent pad 61 to the intermediate portion of the carrier strip 58 until the sample sensor 18 disposed opposite the intermediate portion of the carrier strip 58 detects the presence of the sample due to the change in color of the wetted porous carrier strip 58. In this regard, an illuminating light-emitting diode (LED) 67 disposed on the underside of the printed circuit board 19 between the sensors 18 and 23 illuminate the intermediate portion of the porous carrier strip 58 to reflect light therefrom to the sensors. The LED 67 may produce light in the visible range of the electromagnetic spectrum. A white LED is preferred, but a green LED may also be used for the illuminating LED 67, depending on the color of the line formed on the test strip 16.

Thus, in the present example, as a pregnancy test, no control line is required. Additionally, the reaction forms a complex produced by bonding between a white latex particle and a marking element in the form of colloidal gold to the antigen HCG.

Considering now the housing 12 in greater detail, the housing 12 includes a bottom portion 69, which is secured to a top portion 72 for enclosing the printed circuit board 19 with its components as well as the test strip 16. When the device 10 is employed as a multiple use device, the housing 12 can be disassembled as indicated in FIG. 2 to permit the test strip 16 to be replaced by a fresh test strip for performing additional tests. The insulator strip 49 of the switch actuator 47 may be in the form of a rigid strip of suitable materials such as thermal plastic or other such material. In this regard, the insulator strip 49 can be reinserted through the opening 52 and under the battery 43 to disengage it electrically from the printed circuit board 19.

Considering now the switch actuator 47 with reference to FIGS. 4 and 6 of the drawings, the actuator 47 includes a u-shaped spring mounting device 74 which serves as a conductor and surmounts the battery 43 and positions it opposite to a circuit board negative contact 78. The top portion of the mounting device or contact 74 is dimpled at 76 to engage the positive surface of the battery 43 electrically to provide electrical contact between the positive terminal of the battery 43 and a positive terminal 81 on the printed circuit board 19. The insulator strip 49 is adapted to be positioned between the negative terminal of the battery 43 and the circuit board contact 78 as shown in FIG. 4 to disengage electrically the battery 43 from the printed circuit board 19. When the lid 14 is removed, the insulator strip 49 is fixed at one of its ends to the lid 14 and its opposite end is pulled out from between the underside of the battery 43 and the circuit board contact 78. This causes the battery 43 to have its negative terminal snap into engagement with the contact 78 due to the spring tension of the spring mounting device 74.

Considering now the electrical circuit for the device 10 with reference to FIG. 7, when the switch 45 is closed by removing the strip 47, the battery 43 is connected across a capacitor 83, and a parallel combination with the illuminating LED 67 connected in series with a current limiting resistor 84 so that the LED 67 becomes illuminated once the switch 45 is closed. This current flow is sensed by the processor 21 to cause the amber (LED 27 of FIG. 1) to be energized. In the actual implementation of the circuit as shown in FIG. 7, it is preferred to use a tri-color light-emitting diode (LED) 85 comprising light-emitting diodes 86 and 88 to form the amber, green and red colors corresponding to the amber LED 27, the green LED 29 and the red LED 32 of FIG. 1. When both LEDs 86 and 88 are energized via respective current limiting resistors 87 and 88, the amber light is created. When only one of the two diodes 86 and 88 are illuminated, then either the green or the red light is generated. Also, as will become apparent to those skilled in the art, other illumination devices such, for example, as photo-transistors may also be employed. The LED 85 is energized via a current limiting resistor 89 by the processor 21.

The sensors 18 and 23 in the form of photo-optic photo cells are connected via a voltage divider network including resistors 92 and 94 to provide the threshold levels for the photo cells so that the photo cells will not respond to a change in color unless it exceeds the threshold level so that the device 10 can detect a sufficient amount of the certain substance contained in the test sample.

As will become apparent to those skilled in the art, numerous modifications as well as variations of the disclosed embodiments of the present invention may be made in light of the foregoing teachings. Therefore, it is to be understood that within the scope of the appended claims, the invention may be practiced otherwise as specifically described herein.

What is claimed is:

1. An assay test device for determining whether a fluid under test contains a certain substance, comprising:
    a housing having a top portion and a bottom portion;
    an elongated test strip disposed within said housing, said test strip containing a reagent and adapted to receive a sample of the fluid under test at a sample receiving end portion thereof;
    the elongated test strip including:
        a backing strip having a porous carrier strip overlying the upper surface thereof;
        a fluid absorption strip at one end of the backing strip in fluid communication with porous carrier strip;
        a reagent pad at the opposite end of the backing strip and connected in fluid communication with the wick and the porous carrier strip; and
        an intermediate portion of the porous carrier strip is disposed between the spaced apart absorption strip and the reagent pad;
    an elongated printed circuit board attached to an inner surface of the housing extending substantially parallel to the test strip for mounting electronic components;
    a reaction sensor, an LED, and a sample sensor mounted side by side on one side of the printed circuit board opposite the intermediate portion of the porous carrier strip;
    the sample sensor mounted on said printed circuit board including a gap between the sample sensor and the test strip for detecting the presence of the sample as it flows from the test strip sample receiving end portion using the reflectance at a first position on the test strip for generating a signal indicative of the presence of said sample;
    a processor responsive to the sample presence signal for starting a timer to generate a time delay interval and for generating a time-out signal at the end of the interval;
    the reaction sensor mounted in said printed circuit board and responsive to said time-out signal for detecting the certain substance in the fluid under test received on said test strip using the reflectance at a second position on the test strip to generate an electrical signal indicative of the amount of the substance detected;
    said processor being responsive to said signal from said reaction sensor for generating an output signal indicative of the presence or absence of at least a predetermined quantity of the substance contained in the sample; and
    a display mounted on said housing responsive to said output signal for indicating the presence or absence of a predetermined quantity of the certain substance contained within the fluid under test,
    wherein the sample sensor is a photo-optic sensor.

2. The assay test device according to claim 1, wherein said test strip produces a reaction indication in the presence of the certain substance in the fluid under test.

3. The assay test device according to claim 2, wherein said reaction sensor is a photo-optic sensor to generate the electrical signal indicative of the amount of substance relative to the amount of the photoreflectance of the reaction indication.

4. The assay test device according to claim 1, wherein said processor delays in storing the reaction sensor signal until after a predetermined time delay interval.

5. The assay test device according to claim 4, wherein said processor stores the sensor signal at the completion of the time delay interval, and compares the stored sensor signal with stored threshold electric signals to determine whether or not the fluid under test contains a predetermined quantity of the certain substance.

6. The assay test device according to claim 1, wherein said display includes a display element indicating that the device is ready to receive the fluid under test.

7. The assay test device according to claim 6, wherein said display further includes a positive substance indication display element and a negative substance indication display element.

8. The assay test device according to claim 7, wherein each of said display elements include light emitting diodes.

9. The assay test device according to claim 1, further including a lid removably attached to said housing for covering at least a portion of a fluid receiving end portion of the wick so that said lid can be removed from said housing to expose said fluid receiving end portion of the wick.

10. The assay test device according to claim 9, further including switch means for activating said device, said switch means being responsive to the removal of said lid from said housing.

11. The assay test device according to claim 10, wherein said switch means includes an insulator connected to said lid for deactivating the device, further including a battery for energizing the device, said insulator for connecting electrically the battery.

12. A method of testing a fluid to determine the presence of an analyte comprising:
    introducing the test fluid to the device of claim 1;
    optically sensing the presence of the test fluid at a first position on the intermediate portion of the test strip;
    generating a signal indicative of the presence of the sensed sample;
    starting a time delay interval in response to the signal indicative of the presence of the sensed sample;
    generating a time-out signal at the end of the interval;
    optically sensing a reaction in response to said time-out signal at a second position on the intermediate portion of the test strip;
    determining whether or not the fluid under test contains a the analyte using a processor;
    generating an electric output signal using the processor in response to its determination; and
    indicating the presence or absence of the analyte contained in the fluid under test.

13. The method according to claim 12, wherein following the test the test strip is replaced with a fresh test strip.

14. The method according to claim 13, wherein the test strip is replaced by disassembling a housing at least partially revealing the test strip to permit it to be removed therefrom, and re-assembling the housing with the fresh test strip installed in place.

* * * * *